United States Patent [19]

Inada et al.

[11] Patent Number: 5,120,835
[45] Date of Patent: Jun. 9, 1992

[54] SACCHARIDE DERIVATIVES OF PROTOCATECHUALDEHYDE

[75] Inventors: Kazuyoshi Inada; Sakuo Noda; Fumihiko Kimura, all of Tokyo, Japan

[73] Assignee: Kureha Chemical Industry Co., Ltd., Tokyo, Japan

[21] Appl. No.: 555,064

[22] Filed: Jul. 18, 1990

[30] Foreign Application Priority Data

Aug. 2, 1989 [JP] Japan .................................. 1-200903

[51] Int. Cl.$^5$ ...................... C07C 45/18; A61K 31/11; A61K 31/35
[52] U.S. Cl. ...................................... 536/4.1; 514/825
[58] Field of Search .................... 536/4.1; 514/25, 825

[56] References Cited

U.S. PATENT DOCUMENTS 4,165,341 8/1979 Umemura et al. .................. 568/442
4,578,404 3/1986 Takita et al. ......................... 514/567

Primary Examiner—Ronald W. Griffin
Attorney, Agent, or Firm—Burgess, Ryan & Wayne

[57] ABSTRACT

Novel saccharide derivatives of protocatechualdehyde represented by the general formula (I): t,0010 wherein $R^1$ represents a hydrogen atom or a benzoyl group, and $R^2$ represents an alkyl group.

The method for preparing thereof and the use of the compound as antiinflammatory agents.

31 Claims, 8 Drawing Sheets

SACCHARIDE DERIVATIVES OF PROTOCATECHUALDEHYDE

BACKGROUND OF THE INVENTION

1. Field of the Invention

The present invention relates to the saccharide derivatives of protocatechualdehyde, the method for their preparation, and the use of said derivatives as an anti-inflammatory agent.

2. Description of the Related Art

Recently, protocatechualdehyde is attracting attention as an anti-cancer agent (Japanese Patent Laid-open Publication No. 55-51018), as an anti-inflammatory agent (Japanese Patent Laid-Open Publication No. 58-83619), and as a nephritis remedy (Japanese Patent Laid-open Publication No. 59-196818).

In in-vitro tests, it has proved that protocatechualdehyde, even at a low concentration level, shows a suitable effect of an anti-inflammatory agent that has a pharmacological action of inhibiting leukocytic migration, blood platelet agglutination, and the like; however, in the case of in vivo tests, a large does of protocatechualdehyde must be administered over a long period due to a higher metabolic rate, in order to obtain a significant pharmacological effect, and moreover, the aldehyde portion of the protocatechualdehyde compound poses excitation and oxidizability problems.

SUMMARY OF THE INVENTION

The present inventors, as a result of research and development of a drug which is administered to live organ requiring only a small dosage to show a significant pharmacological effect with the minimum side-effect, have found that this object can be achieved by the novel saccharide derivatives of protocatechualdehyde having its aldehyde portion attached to saccharides.

Consequently, a primary object of the present invention is to provide novel saccharide derivatives of protocatechualdehyde requiring administration of only a small dosage to show favorable pharmacological effects, such as an anti-inflammatory effect, with the minimum side-effect, together with the method for preparation and use of said derivatives. Other objects of the present invention will be evident from what is described below.

BRIEF DESCRIPTION OF THE DRAWINGS

The attached

FIG. 1: Methyl-4,6-O-(3',4'-dibenzoyloxybenzylidene)-α-D-glucopyranoside

FIG. 2: Methyl-4,6-O-(3',4'-dihydroxybenzylidene)-α-D-glucopyranoside

FIG. 3: Methyl-4,6-O-(3',4'-dibenzoyloxybenzylidene)-α-D-galactopyranoside

FIG. 4: Methyl-4,6-O-(3',4'-dihydroxybenzylidene)-α-D-galactopyranoside

FIG. 5: Methyl-4,6-O-(3',4'-dibenzoyloxybenzylidene)-60 -D-mannopyranoside

FIG. 6: Methyl-4,6-O-(3',4'-dihydroxybenzylidene)-α-D-mannopyranoside

FIG. 7: Methyl-4,6-O-(3',4'-dibenzoyloxybenzylidene)-β-D-glucopyranoside

FIG. 8: Methyl-4,6-O-(3',4'-dihydroxybenzylidene)-β-D-glucopyranoside

DETAILED DESCRIPTION OF THE INVENTION

Figure 1:
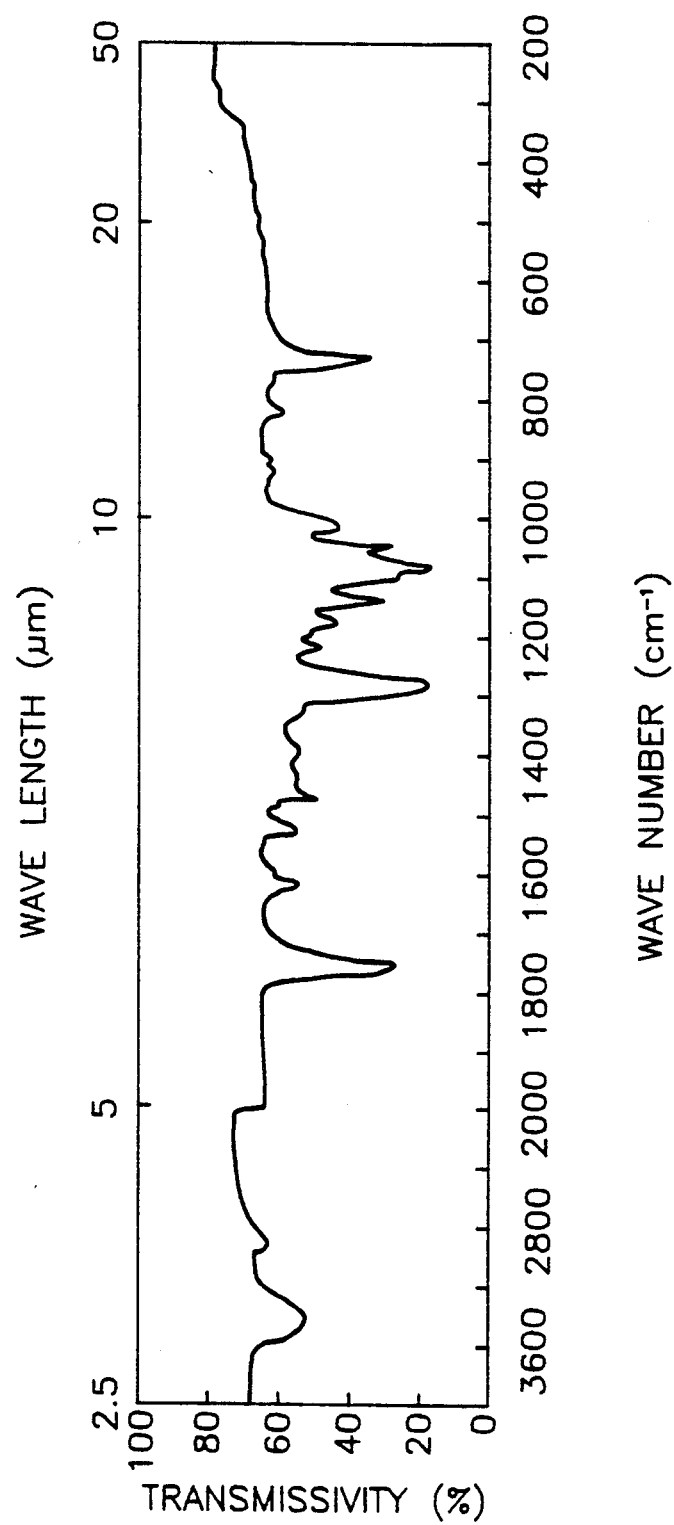
FIG. 1 through FIG. 8 show the infrared absorption spectra of the following compound of the present invention.

The present invention provides novel saccharide derivatives of protocatechualdehyde represented by general formula (I):

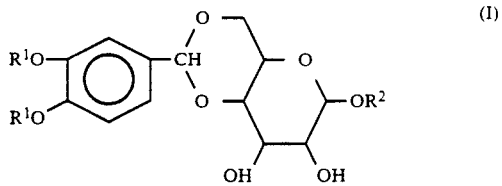

wherein $R^1$ represents a hydrogen atom or a benzoyl group and $R^2$ represents an alkyl group.

The saccharides shown in the above general formula (I) are hexose that includes for example glucose, mannose, galactose, talose, allose, altrose, idose and gulose. Among them, glucose, galactose and mannose are preferable.

$R^2$ represents an alkyl group protecting the hydroxyl group in 1-position of saccharides. Preferably, $R^2$ represents an alkyl group containing 1 to 4 carbon atoms, more preferably 1 to 2 carbon atoms.

The saccharide derivatives of protocatechualdehyde of the present invention represented by the above general formula (I) include, for example, the following compounds:

Methyl-4,6-O-(3',4'-dibenzoyloxybenzylidene)-α-D-glucopyranoside ($Ia_1$)

Methyl-4,6-O-(3',4'-dihydroxybenzylidene)-α-D-glucopyranoside ($Ib_1$)

Methyl-4,6-O-(3',4'-dibenzoyloxybenzylidene)-β-D-glucopyranoside ($Ia_2$)

Methyl-4,6-O-(3',4'-dihydroxybenzylidene)-β-D-glucopyranoside ($Ib_2$)

Methyl-4,6-O-(3',4'-dibenzoyloxybenzylidene)-α-D-galactopyranoside ($Ia_3$)

Methyl-4,6-O-(3',4'-dihydroxybenzylidene)-α -D-galactopyranoside ($Ib_3$)

Methyl-4,6-O-(3',4'-dibenzoyloxybenzylidene)-β-D-galactopyranoside ($Ia_4$)

Methyl-4,6-O-(3',4'-dihydroxybenzylidene)-β-D-galactopyranoside ($Ib_4$)

Methyl-4,6-O-(3',4'-dibenzoyloxybenzylidene)-α-D-mannopyranoside ($Ia_5$)

Methyl-4,6-O-(3',4'-dihydroxybenzylidene)-α-D-mannopyranoside ($Ib_5$)

Methyl-4,6-O-(3',4'-dibenzoyloxybenzylidene)-β-D-mannopyranoside ($Ia_6$)

Methyl-4,6-O-(3',4'-dihydroxybenzylidene)-β-D-mannopyranoside ($Ib_6$)

Methyl-4,6-O-(3',4'-dibenzoyloxybenzylidene)-α-D-glucopyranoside ($Ia_7$)

Ethyl-4,6-O-(3',4'-dihydroxybenzylidene)-α-D-glucopyranoside ($Ib_7$)

n-propyl-4,6-O-(3',4'-dibenzoyloxybenzylidene-60 -D-glucopyranoside ($Ia_8$)

n-propyl-4,6-O-(3',4'-dibenzoyloxybenzylidene-60 -D-glucopyranoside ($Ib_{81}$)

i-propyl-4,6-O-(3',4'-dibenzoyloxybenzylidene-60 -D-glucopyranoside ($Ia_9$)

i-propyl-4,6-O-(3',4'-dibenzoyloxybenzylidene-60 -D-glucopyranoside ($Ib_9$)

n-butyl-4,6-O-(3',4'-dibenzoyloxybenzylidene-β-D-glucopyranoside (Ia₁₀)
n-propyl-4,6-O-(3',4'-dihydroxybenzylidene-β-D-glucopyranoside (Ib₁₀)
The structural formulae of the above compounds are shown below, wherein the code numbers used for the compounds (Ia₁, Ib₁, ... Ia₁₀, Ib₁₀) correspond to the same code numbers used for the structural formulae.
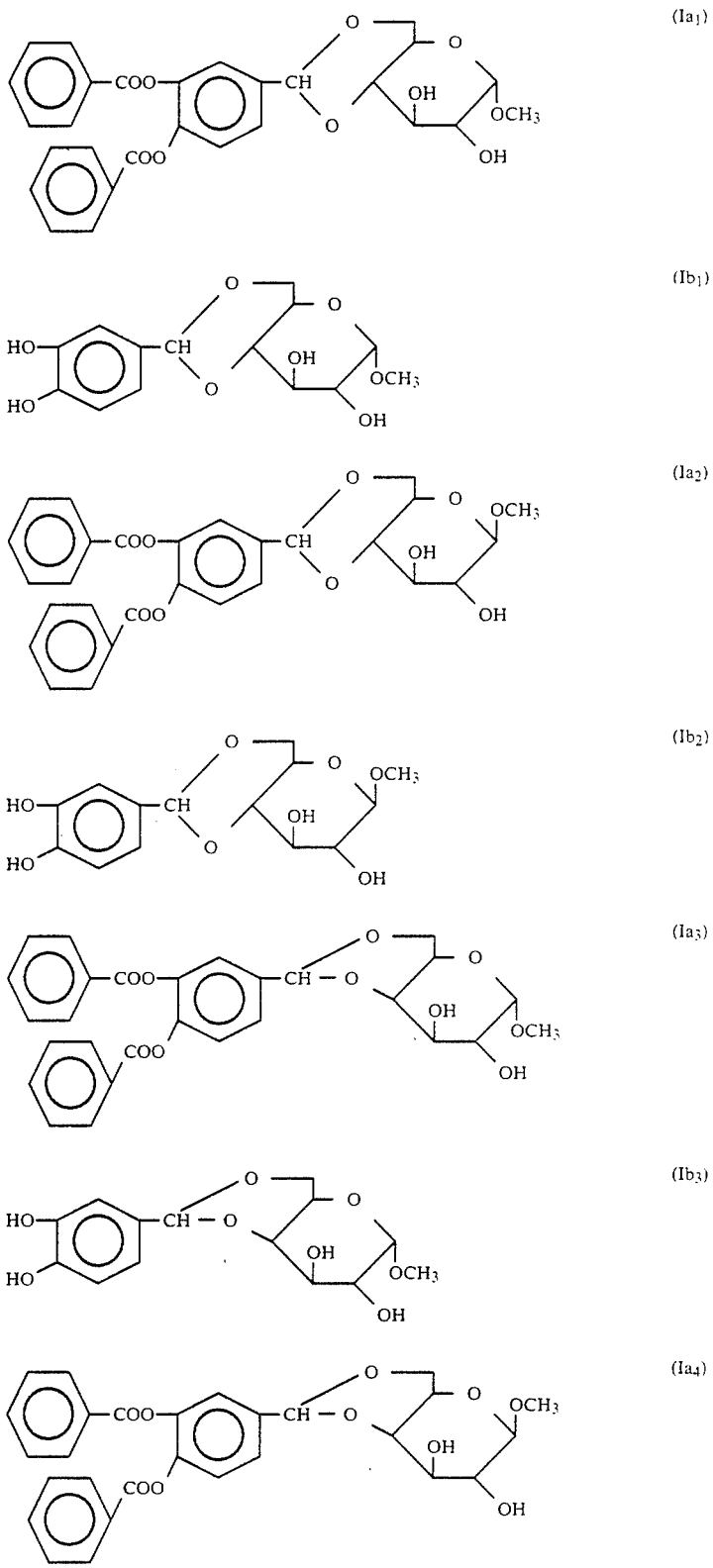

-continued
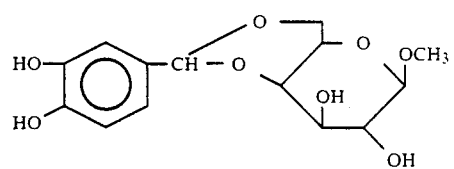 (Ib₄)
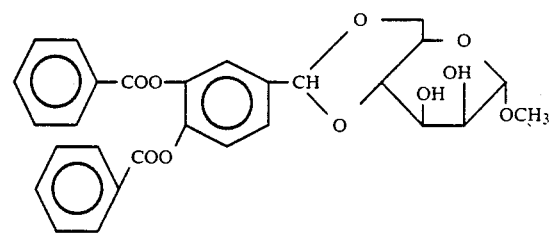 (Ia₅)
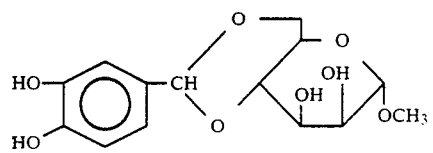 (Ib₅)
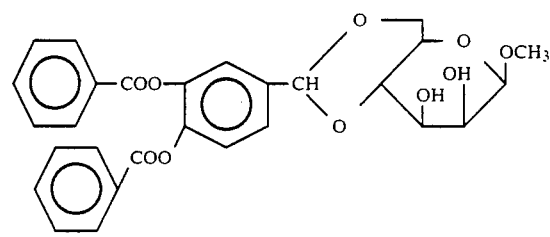 (Ia₆)
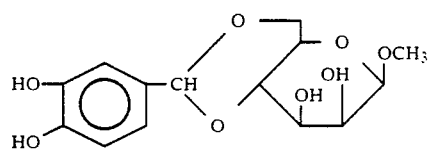 (Ib₆)
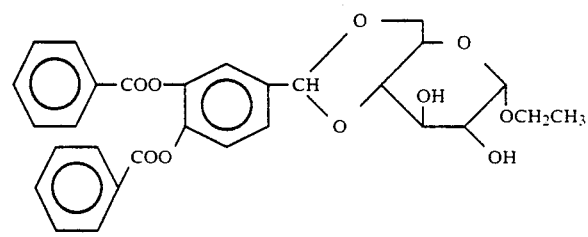 (Ia₇)
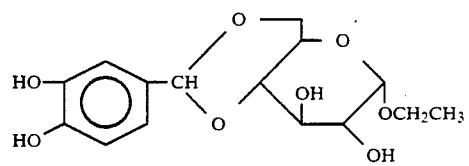 (Ib₇)
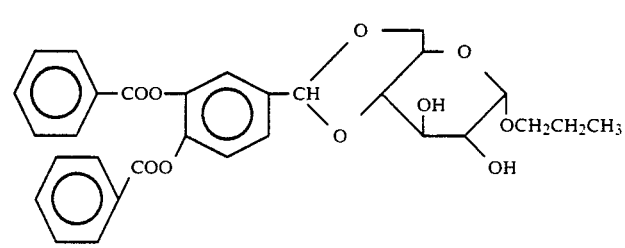 (Ia₈)

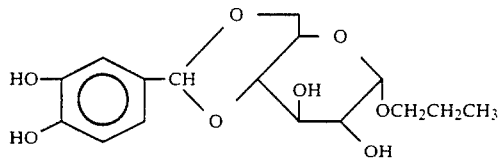 (Ib₈)

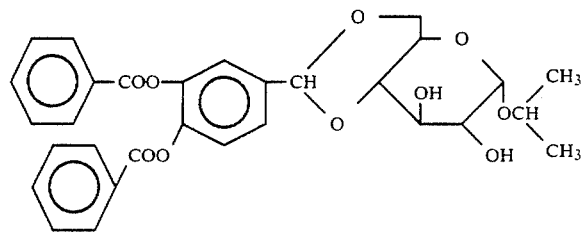 (Ia₉)

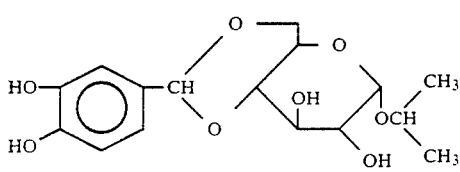 (Ib₉)

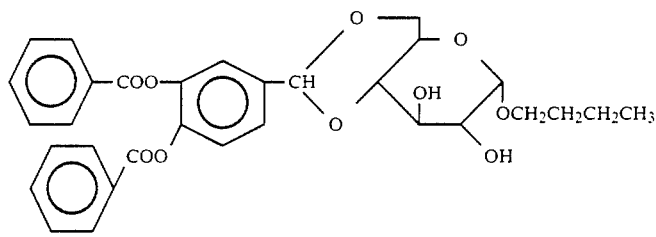 (Ia₁₀)

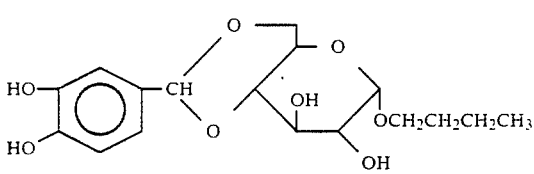 (Ib₁₀)

The saccharide derivatives of protocatechualdehyde of the present invention may be α-form, β-form, or mixtures thereof. The saccharides in the derivatives of the present invention may be D-form, L-form or mixtures thereof.

The saccharide derivatives of protocatechualdehyde of the present invention (hereinafter called compounds of the present invention) can be produced advantageously by the following method.

By reacting the acetalized compound (V) derived from acetalization of 3,4-dibenzoyloxybenzaldehyde (II) by using lower alcohol (IV), with the saccharide derivative represented by general formula (III):

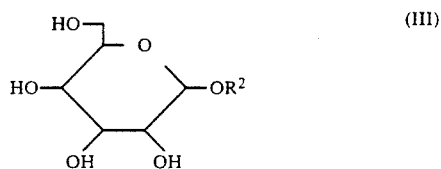 (III)

wherein $R^2$ represents an alkyl group, compound (Ia) of the present invention, which has a benzoyl group as $R^1$ in general formula (I), is obtained, and further by ammonolysis, compound (Ib) of the present invention,
which has a hydrogen atom as $R^1$ in general formula (I), is obtained.

The reaction route for the synthesis of the saccharide derivatives of protocatechualdehyde of the present invention are shown below.

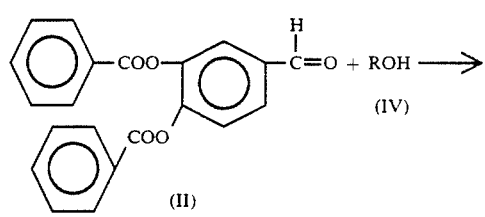

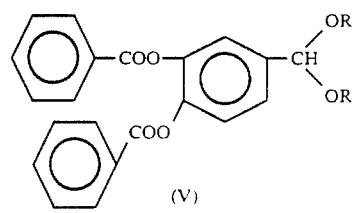

-continued

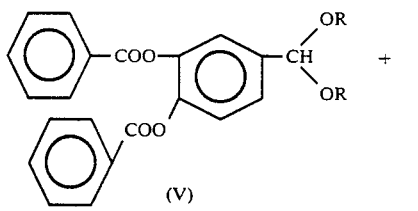

(V)

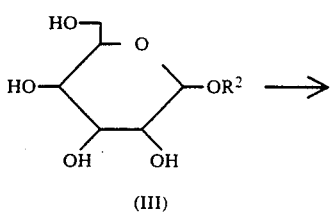

(III)

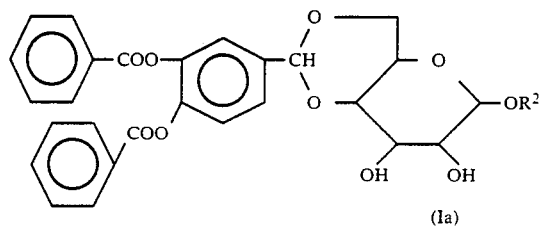

(Ia)

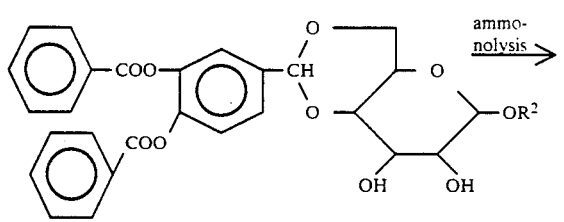

(Ia)

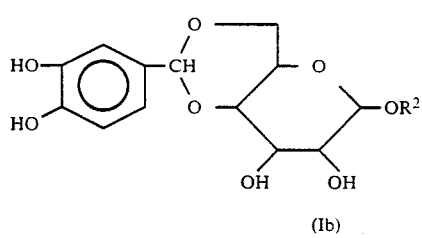

(Ib)

The acetalization of the above method for preparing (V) is carried out by dissolving 3,4-dibenzoyloxybenzaldehyde (II) in a lower alcohol (IV) such as methanol or ethanol, then by adding a catalytic amount of p-toluenesulfonic acid or the like and by heating the mixture for 2 to 5 hours under reflux. From the reaction mixture, the lower alcohol (IV) is evaporated, and the residue, or the acetalized compound (V) isolated from the said residue, is reached with the saccharide derivatives (III).

The said saccharide derivatives include, for example, 1-O-methyl-α-D-glucopyranoside, 1-O-methyl-β-D-glucopyranoside 1-O-methyl-α-D-galactopyranoside 1-O-methyl-α-D-mannopyranoside, 1-O-methyl-β-D-mannopyranoside, 1-O-ethyl-α-D-glucopyranoside, 1-O-n-propyl-α-D-glucopyranoside, 1-O-i-propyl-α-D-glucopyranoside, and 1-O-n-butyl-α-D-glucopyranoside.

Acetalized compounds of 3,4-dibenzoyloxybenzaldehyde (II) is reacted with saccharide derivatives (III) in an organic solvent in the presence of an acid catalyst at 55°–65° C., and this temperature is eventually raised to 80°–100° C., while the alcoholic content which is set free is separated and removed and the solvent is refluxed under reduced pressure. Although any organic solvent that does not affect the reaction can be used, usually absolute dimethylformamide or the like is used. As the acid catalyst, p-toluenesulfonic acid or the like is used. After the completion of the reaction, the compound (Ia) of the present invention is obtained by evaporating the organic solvent under reduced pressure, then dissolving the residue in an organic solvent such as ethyl acetate or the like, removing the acid catalyst through washing with a saturated sodium bicarbonate aqueous solution or the like, further removing the organic solvent if necessary, and finally, purifying the product through recrystallization or the like.

The compound (Ib) of the present invention is obtained by the ammonolysis of the compound (Ia) of the present invention. The ammonolysis is carried out by suspending the compound (Ia) of the present invention in an alcohol such as absolute methanol and then bubbling ammonia gas into the mixture at the room temperature. The ammonia gas is bubbled in slowly to keep the temperature from rising by heat generation.

The 3,4-dibenzoyloxybenzaldehyde (II) used as a starting material is obtained by dissolving, for example, protocatechualdehyde and triethylamine in dichloromethane and then adding benzoyl chloride dropwise while stirring in an icy water bath.

Next, the medical applications of the compounds of the present invention are illustrated.

The compounds of the present invention can be administered orally, intra-intestinally, or by injection in a variety of pharmaceutical preparation forms and formulations combined with medically recognized carriers and/or adjuvants. In this case, two or more compounds of the present invention may be used together in a mixture, or may be used by combining with any other pharmaceutically active component.

As the compounds of the present invention can be administered orally or non-orally, it is possible to take different drug forms suitable for respective administration modes. Furthermore, the compounds of the present invention can be supplied on an administration unit form, wherein as long as an effective dosage is contained, a variety of preparation forms are permissible, such as powder, granule, tablet, sugar coated tablet, capsule, suppository, suspension, fluid, emulsion, ampule and injection forms.

Consequently, the drugs of the present invention should be understood as suppliable in any known form of pharmaceutical preparation. The content of compounds of the present invention (active component) in the preparation of the present invention can vary widely from 0.01 to 100%, preferably from 0.1 to 70% (by weight).

As above-mentioned, the drugs of the present invention is administered to humans and animals orally or non-orally. In this case, oral administration includes sublingual administration, and non-oral administration includes subcutaneous, intramuscular and intravenous injections and drip infusions.

As the dosage of the drugs of the present invention varies according to the subject (animal or human), age, individual variation, disease conditions and the like, the drug of the present invention may be administered in an amount outside the range of the dosage indicated below, but in the case of humans, the general oral dosage of compounds of the present invention is 0.1–500 mg per 1 kg of weight per day, preferably 0.5–200 mg, and the general non-oral dosage is 0.01–200 mg per 1 kg of weight per day, preferably 0.1–100 mg, wherein the daily amount is administered in 1–4 divided dosages.

As stated above, the compounds of the present invention are novel compounds having an inhibiting activity against granuloma growth, a lower toxicity then protocatechualdehyde, and a pharmaceutical effect even with a small dosage.

Consequently, the compound of the present invention are suitable as an anti-inflammatory agent for the remedy of chronic articular rheumatism and the like when administered singly or as an active component of pharmaceutical preparations.

The present invention is further illustrated by following examples.

EXAMPLE 1

(1) Synthesis of 3,4-dibenzoyloxybenzaldehyde 69 g of protocatechualdehyde and 111 g of triethylamine were dissolved in a 1,500 ml of dichloromethane, then 141 g of benzoyl chloride was added dropwise into the solution during a 40 minute period under stirring in a icy water bath. After the dripping, the resultant mixture was stirred for 3 hours at the room temperature. The reaction mixture was washed with 1,000 ml of water, with 1,000 ml of 1N hydrochloric acid and then with 1,000 ml of water. The resultant dichloromethane layers were dehydrated and dried with magnesium sulfate, then the dichloromethane was evaporated, and the residue was recrystallized from benzene/hexane and further recrystallized from methanol; finally, 107 g of 3,4-dibenzoyloxybenzaldehyde (62% yield) was obtained in the form of crystals having melting point at 101.0°–101.8° C. The elementary analysis value of this product was as follows:

Elementary Analysis Value: Found (%): C, 72.8, H, 4.0. Calculated (%): C, 72.8, H, 4.0.

(2) Acetalization of 3,4-dibenzoyloxybenzaldehyde 18.5 g of the above 3,4-dibenzoyloxybenzaldehyde and 0.35 g of p-toluenesulfonic acid were dissolved in a 150 ml of absolute methanol, and after heated for 4 hours under reflux, the methanol was evaporated at 40° C. under reduced pressure.

The evaporating process was continued for an additional 10 minutes after methanol had distilled off. Further attempts were made to remove any remainihg methanol by reducing the pressure with a vacuum pump at the room temperature. Although containing a small amount of non-reacted 3,4-dibenzoyloxybenzaldehyde, the residue was used in the next reaction process.

(3) Synthesis of Methyl-4,6-O-(3',4'-dibenzoyloxybenzylidene)-α-D-glucopyranoside 11 g of 1-O-methyl-α-D-glucopyranoside and 0.3 g of p-toluenesulfonic acid were added to the residue obtained in the above (2), then the mixture was dissolved in 90 ml of dimethylformamide. The pressure reduction using a rotary evaporator was adjusted in such a way that dimethylformamide was maintained in a reflux state in a water bath of 60°– 65° C., and the reaction was maintained for one hour. Then, the water bath temperature was raised to 85° C. to evaporate dimethylformamide under reduced pressure, and the same temperature level was maintained for an additional 10 minutes after the termination of the dimethylformamide distillation. Then, the residue was dissolved in a 300 ml ethyl acetate, and this solution was washed 2 times with 200 ml saturated aqueous solution of sodium hydrogencarbonate, then 2 times with 200 ml saturated aqueous solution of sodium chloride. The resultant ethyl acetate layer was dehydrated with magnesium sulfate, and then the ethyl acetate was evaporated under reduced pressure. The residue was recrystallized from methanol and was further recrystallized from ethyl acetate/n-hexane; finally, 13.9 g of methyl-4,6-O-(3',4'-dibenzoyloxybenzylidene)-α-D-glucopyranoside (50% yield) was obtained in the form of crystals having melting point at 152°–153° C. (in a vacuum sealed tube). The angle of optical rotation, elementary analysis value, infrared absorption spectrum (IR) and $^1$H nuclear magnetic resonance spectrum ($^1$H-NMR) of this product were as follows:

Angle of optical rotation: $[\alpha]_D^{23.0} = +60°$ (c 1.0, acetone)

Elementary Analysis Value: Found (%): C, 64.1, H, 5.0. Calculated (%): C, 64.4, H, 5.0.

IR (KBr tablet): Shown in FIG. 1.

$^1$H-NMR (d-acetone, TMS internal standard, ppm): 7.4–8.1 (13H), 5.71 (1H), 4.73 (1H), 4.25 (1H), 3.7–3.9 (3H), 3.4–3.6 (5H)

(4) Synthesis of Methyl-4,6-O-(3',4'-dihydroxybenzylidene)-α-D-glucopyranoside 10.8 g of methyl-4,6O-(3',4'-dibenzoyloxybenzylidene-α-D-glucopyranoside obtained in the above (3) was suspended in 100 ml of absolute methanol, and ammonia gas was bubbled into the suspension to undergo an ammonolysis at the room temperate. The bubbling of ammonia gas was carried out at such a slow pace that the temperature was kept from rising due to a heat generation, and was continued until the heat generation terminated. Then methanol was evaporated under reduced pressure. The sampling of this residue indicated the formation of a compound having an approximate Rf value of 0.3 under silica gel thin layer chromatography (solvent: acetone/ethyl acetate ⅓ v/v) and turning black when sprayed with alcoholic solutions of ferric chloride. The compounds in question were isolated from the residue by a silica gel column chromatography (solvent: acetone/ethyl acetate ⅓ v/v), and were recrystallized from ethyl acetate; finally, 4.4 g of methyl-4,6-O-(3',4'-dihydroxybenzylidene)-α-D-glucopyranoside (68% yield) was obtained in the form of crystals having melting point (decomposed) at 172.5°–175.5° C. (in a vacuum sealed tube). The angle of optical rotation, elementary analysis value, infrared absorption spectrum (IR), and $^1$H nuclear magnetic resonance spectrum ($^1$H-NMR) of this product were as follows:

Angle of optical rotation: $[\alpha]_D^{23.5} = +80.0°$ (c 1.0, methanol)

Elementary Analysis Value: Found (%): C, 53.3, H, 6.0. Calculated (%): C, 53.5, H, 5.7.

Figure 2:
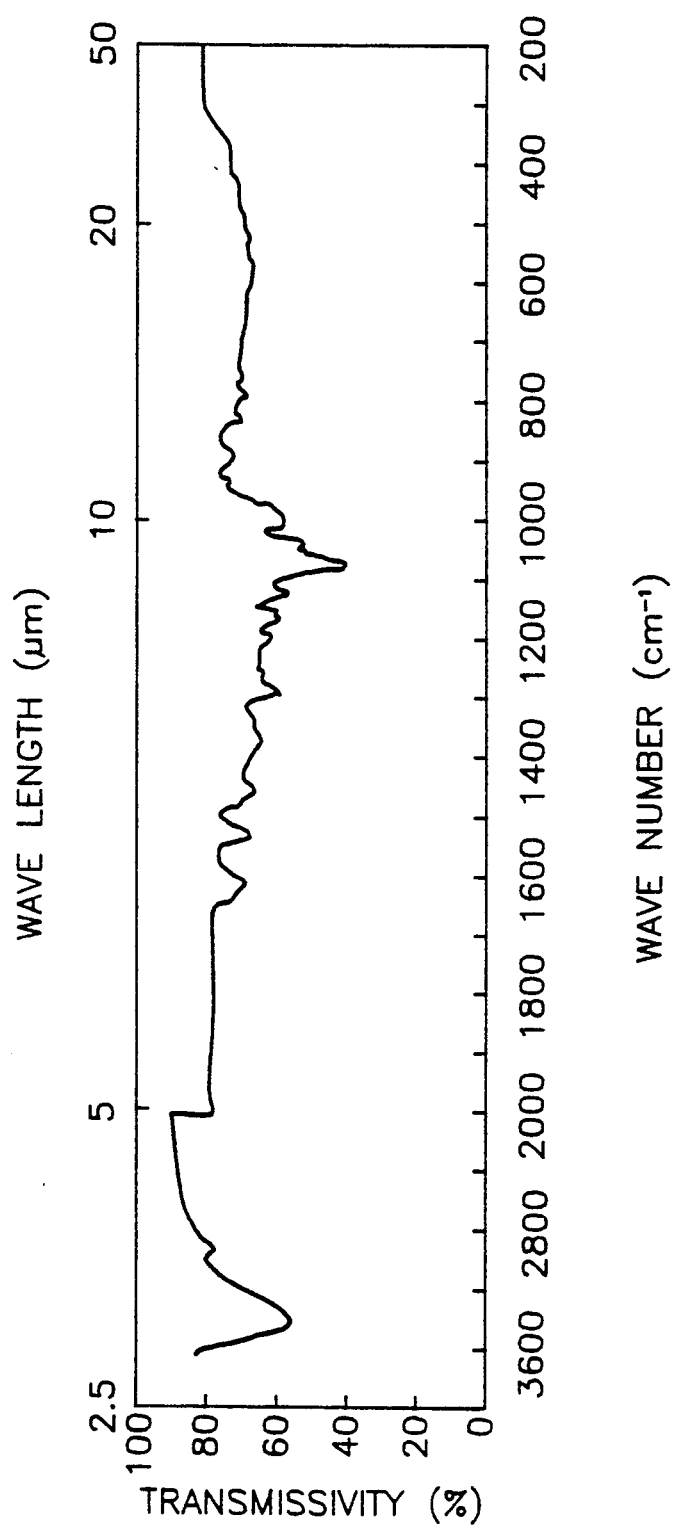

IR (KBr tablet): Shown in FIG. 2.

$^1$-NMR (d-acetone, TMS internal standards, ppm): 6.7–7.0 (3H), 5.42 (1H), 4.71 (1H), 4.14 (1H), 3.6–3.8 (3H), 3.3–3.5 (5H).

EXAMPLE 2

(1) Synthesis of Methyl-4,6-O-(3',4'-dibenzoyloxybenzylidene)-α-D-galactopyranoside The residue derived from acetalization of 20 g of 3,4-dibenzoyloxybenzaldehyde in the same manner as Example 1(2) was reacted with 11.3 g of 1-O-methyl-α-D-galactopyranoside in the same manner as Example 1(3) and upon after-treatment, the residue derived from evaporation of ethyl acetate was recrystallized from methanol, and was further recrystallized from ethyl acetate; finally, 14.1 g of methyl-4,6-O-(3',4'-dibenzoyloxybenzylidene)-α-D-galactopyranoside (47% yield) was obtained in the form of crystals having melting point at 186.5°–187.5° C. (in a vacuum sealed tube). The angle of optical rotation, elementary analysis value, infrared absorption spectrum (IR), and $^1$H nuclear magnetic resonance spectrum ($^1$H-NMR) of this product were as follows:

Angle of optical rotation: $[\alpha]_D^{23.5} = +84.4°$ (c 1.0, acetone)

Elementary Analysis Value: Found (%): C,64.3, H,5.0. Calculated (%): C,64.4, H,5.0.

Figure 3:
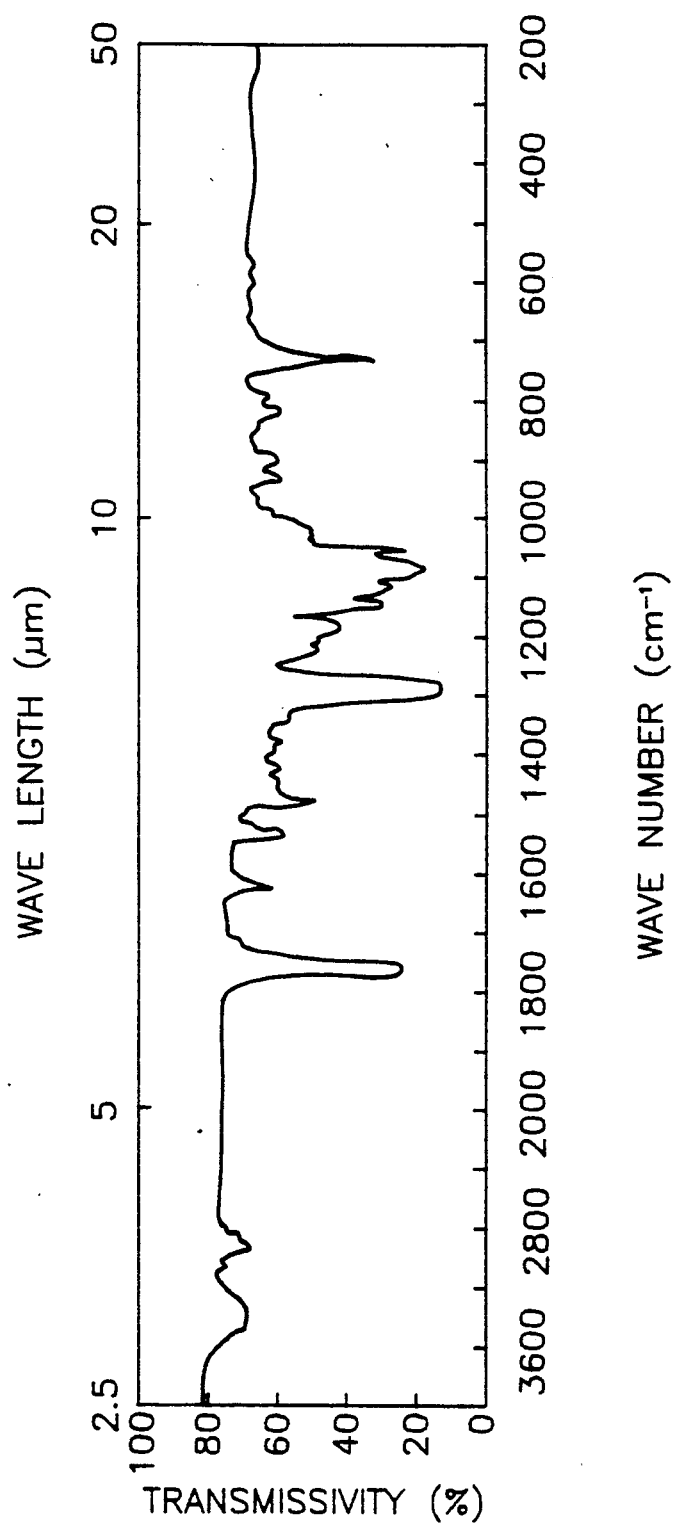

IR (KBr tablet): Shown in FIG. 3.

$^1$H-NMR (d-acetone, TMS internal standards, ppm): 7.4–8.1 (13H), 5.73 (1H), 4.75 (1H), 4.32 (1H), 4.1–4.2 (2H), 3.7–3.9 (3H), 3.39 (3H).

(2) Synthesis of Methyl-4,6-O-(3',4'-dihydroxybenzylidene)-α-D-galactopyranoside As in Example 1(4), an ammonolysis was carried out by using 14.0 g of the methyl-4,6-O-(3',4'-dibenzoyloxybenzylidene)-α-D-galactopyranoside obtained in the above (1). The residue derived from evaporation of methanol was applied with a silica gel column chromatography (solvent: acetone/ethyl acetate ⅓ v/v), and the portion stained with ferric chloride of silica gel thin-layer chromatography (Rf value of 0.2–0.25) was isolated; then, this portion was recrystallized from acetone/benzene, and finally, 4.9 g of methyl-4,6-O-(3',4'-dibenzoyloxybenzylidene)-α-D-galactopyranoside (58% yield) was obtained in the form of crystals having melting point (decomposed) at 110°–113° C. (in a vacuum sealed tube). The angle of optical rotation, elementary analysis value, infrared absorption spectrum (IR), and $^1$H nuclear magnetic resonance spectrum ($^1$H-NMR) of this product were as follows:

Angle of optical rotation: $[\alpha]_D^{23.7} = +147°$ (c 1.0, methanol)

Elementary Analysis Value: Found (%): C,53.3, H,5.9. Calculated (%): C,53.5, H,5.7.

Figure 4:
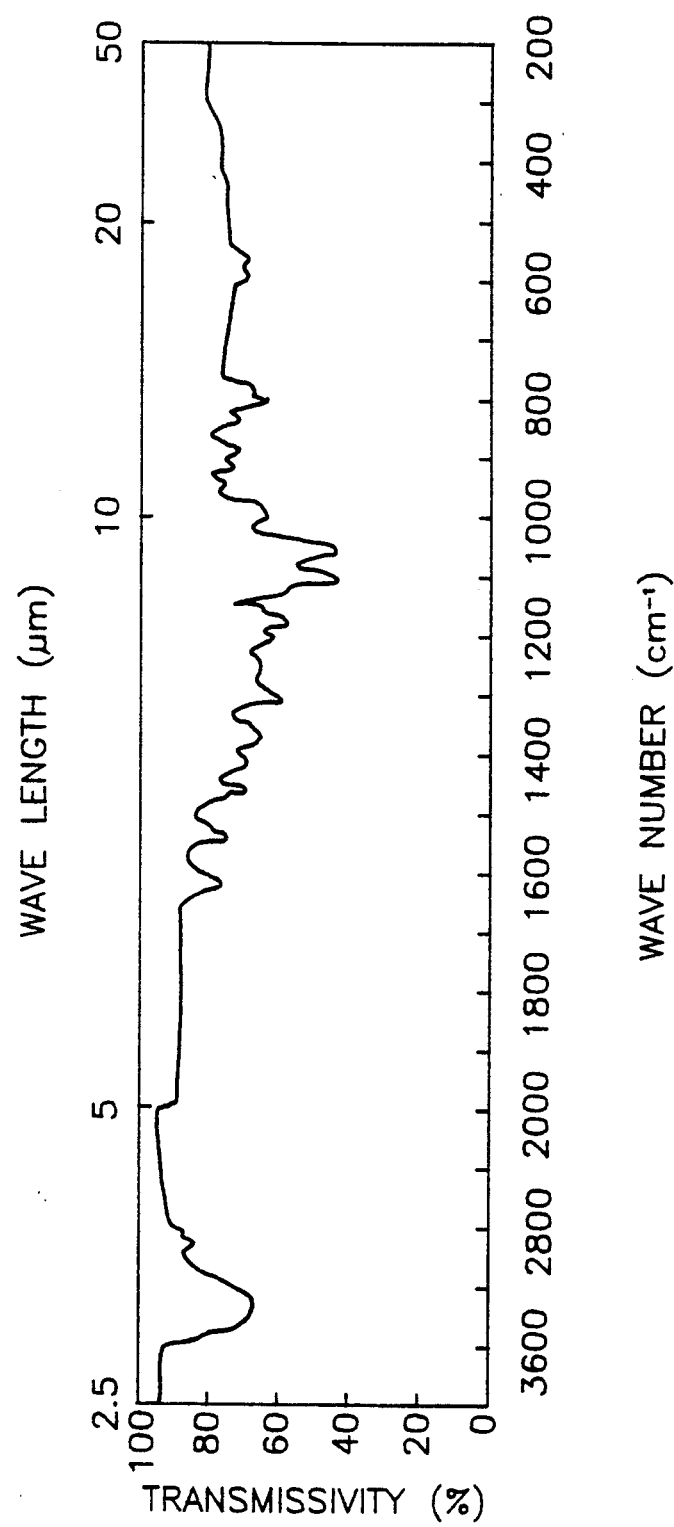

IR (KBr tablet): Shown in FIG. 4.

$^1$H-NMR (d-acetone, TMS internal standards, ppm): 6.7–7.0 (3H), 5.44 (1H), 4.74 (1H), 4.0–4.3 (3H), 3.8–3.9 (2H), 3.66 (1H), 3.39 (3).

EXAMPLE 3

(1) Synthesis of Methyl-4,6-O-(3',4'-dibenzoyloxybenzylidene)-α-D-mannopyranoside The residue derived from acetalization of 10 g of 3,4-dibenzoyloxybenzaldehyde in the same manner as Example 1(2) was reacted with 5.6 of 1-O-methyl-α-D-mannopyranoside in the same manner as Example 1(3), and upon after-treatment, before recrystallization, the residue derived from evaporation of ethyl acetate was isolated by a silica gel column chromatography (solvent: benzene/ethyl acetate 7/3 v/v), then recrystallized from benzene/cyclohexane; finally, 6.1 g of methyl-4,6-O-(3',4'-dibenzoyloxybenzylidene)-α-D-mannopyranoside (40% yield) was obtained in the form of crystals having melting point at 166.0°–166.7° C. (in a vacuum sealed tube). The angle of optical rotation, elementary analysis value, infrared absorption spectrum (IR), and $^1$H nuclear magnetic resonance spectrum ($^1$H-NMR) of this product were as follows:

Angle of optical rotation: $[\alpha]_D^{23.5} = +28.4°$ (c 1.0, acetone)

Elementary Analysis Value: Found (%): C,64.1, H,4.9. Calculated (%): C,64.4, H,5.0.

Figure 5:
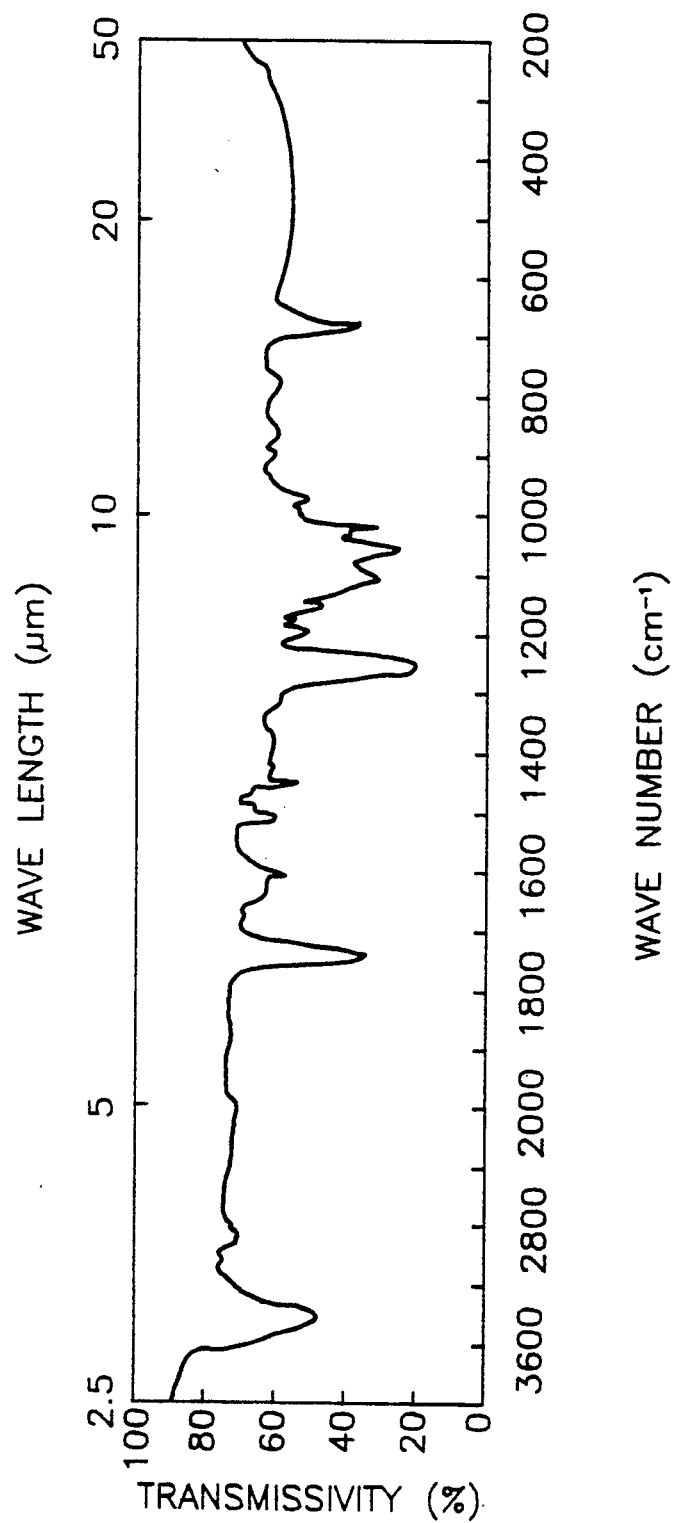

IR (KBr tablet): Shown in FIG. 5.

$^1$H-NMR (d-acetone, TMS internal standards, ppm): 7.4–8.1 (13H), 5.73 (1H), 4.71 (1H), 4.23 (1H), 3.7–4.0 (5H), 3.38 (3H).

(2) Synthesis of Methyl-4,6-O-(3',4'-dihydroxybenzylidene)-α-D-mannopyranoside

As in Example 1(4), an ammonolysis was carried out by using 3.83 g of the methyl-4,6-O-(3',4'-dibenzoyloxybenzylidene)-α-D-mannopyranoside obtained in the above (1). The residue derived from evaporation of methanol was applied with a silica gel column chromatography (solvent: benzene/ethyl acetate ½ v/v), and the portion stained with ferric chloride of silica gel thin-layer chromatography (Rf value of about 0.2) was isolated; then, this portion was dissolved in a thermal acetone, and was crystallized by gradually adding benzene; finally, 1.69 g of methyl-4,6-O-(3',4'-dihydroxybenzylidene)-α-D-mannopyranoside (73% yield) was obtained in the form of crystals having melting point (decomposed) at 120.5°–123.0° C. (in a vacuum sealed tube). The angle of optical rotation, elementary analysis value, infrared absorption spectrum (IR), and $^1$H nuclear magnetic resonance spectrum ($^1$H-NMR) of this product were as follows:

Angle of optical rotation: $[\alpha]_D^{23.5} = +32°$ (c 1.0, methanol)

Elementary Analysis Value: Found (%): C,53.4, H,5.7. Calculated (%): C,53.5, H,5.7.

Figure 6:
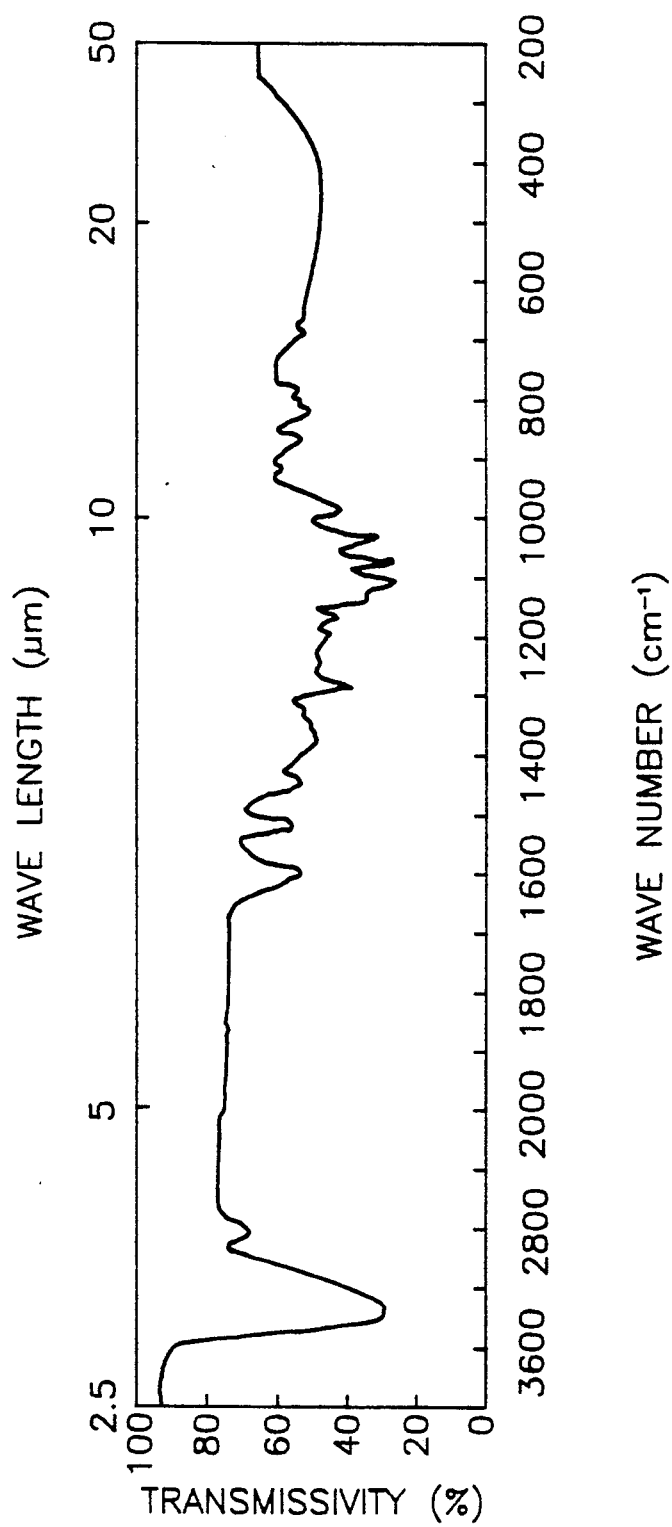

IR (KBr tablet): Shown in FIG. 6.

$^1$H-NMR (d-acetone, TMS internal standards, ppm): 6.7–7.0 (3H), 5.44 (1H), 4.68 (1H), 4.13 (1), 3.6–3.9 (5H), 3.37 (3H).

EXAMPLE 4

(1) Synthesis of Methyl-4,6-O-(3',4'-dibenzoyloxybenzylidene)-β-D-glucopyranoside The residue derived from acetalization of 8 g of 3,4-dibenzoyloxybenzaldehyde in the same manner as Example 1(2) was reacted with 4.48 g of 1-O-methyl-β-D-glucopyranoside in the same manner as Example 1(3), and upon after-treatment, the residue derived from evaporation of ethyl acetate was recrystallized from methanol, and further recrystallized from ethyl acetate/n-hexane; finally, 5.23 g of methyl-4,6-O-(3',4'-dibenzoyloxybenzylidene)-β-D-glucopyranoside (43% yield) was obtained in the form of crystals having melting point at 182°–184° C. (in a vacuum sealed tube). The angle of optical rotation, elementary analysis value, infrared absorption spectrum (IR), and $^1$H nuclear magnetic resonance spectrum (¹H-NMR) of this product were as follows:

Angle of optical rotation: $[\alpha]_D^{23.5} = +-44.0°$ (c 1.0, acetone)

Elementary Analysis Value: Found (%): C,64.1, H,5.0. Calculated (%): C,64.4, H,5.0.

Figure 7:
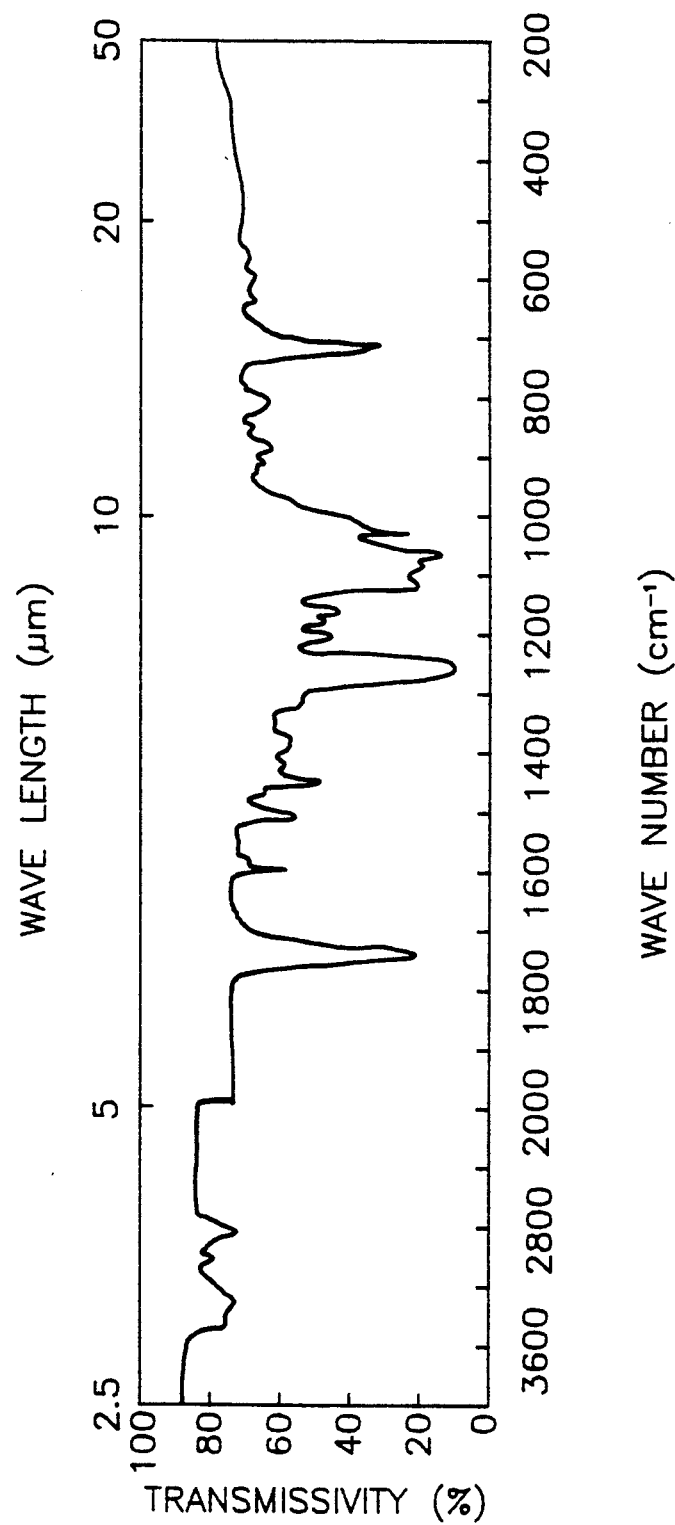

IR (KBr tablet): Shown in FIG. 7.

¹H-NMR (d-acetone, TMS internal standards, ppm): 7.4–8.1 (13H), 5.72 (1H), 4.2–4.4 (2H), 3.80 (1H), 3.69 (1H), 3.4–3.6 (5H), 3.32 (1H).

(2) Synthesis of Methyl-4,6-O-(3',4'-dihydroxybenzylidene)-β-D-glucopyranoside As in Example 1(4), an ammonolysis was carried out by using 4.15 g of the methyl-4,6-O-(3',4'-dibenzoyloxybenzylidene)-β-D-glucopyranoside obtained in the above (1). the residue derived from evaporation of methanol was isolated by a silica gel column chromatography. Ethyl acetate/benzene (3/1 v/v) was first used as the solvent, then acetone was used. The portion stained with ferric chloride of silica gel thin-layer chromatography (approximate Rf value of 0.3) was isolated (crude yield: 2.3 g), and then, this portion was recrystallized from acetone/benzene (1/1 v/v); finally, 1.56 g of methyl-4,6-O-(3',4'-dihydroxybenzylidene)-β-D-glucopyranoside (62% yield) was obtained in the form of crystals having melting point (decomposed) at 175.5°–178.0° C. (in a vacuum sealed tube). The angle of optical rotation, elementary analysis value, infrared absorption spectrum (IR), and ¹H nuclear magnetic resonance spectrum (¹H-NMR) of this product were as follows:

Angle of optical rotation: $[\alpha]_D^{23.5} = -74.4°$ (c 1.0, methanol)

Elementary Analysis Value: Found (%): C,53.4, H,5.8. Calculated (%): C,53.5, H,5.7.

Figure 8:
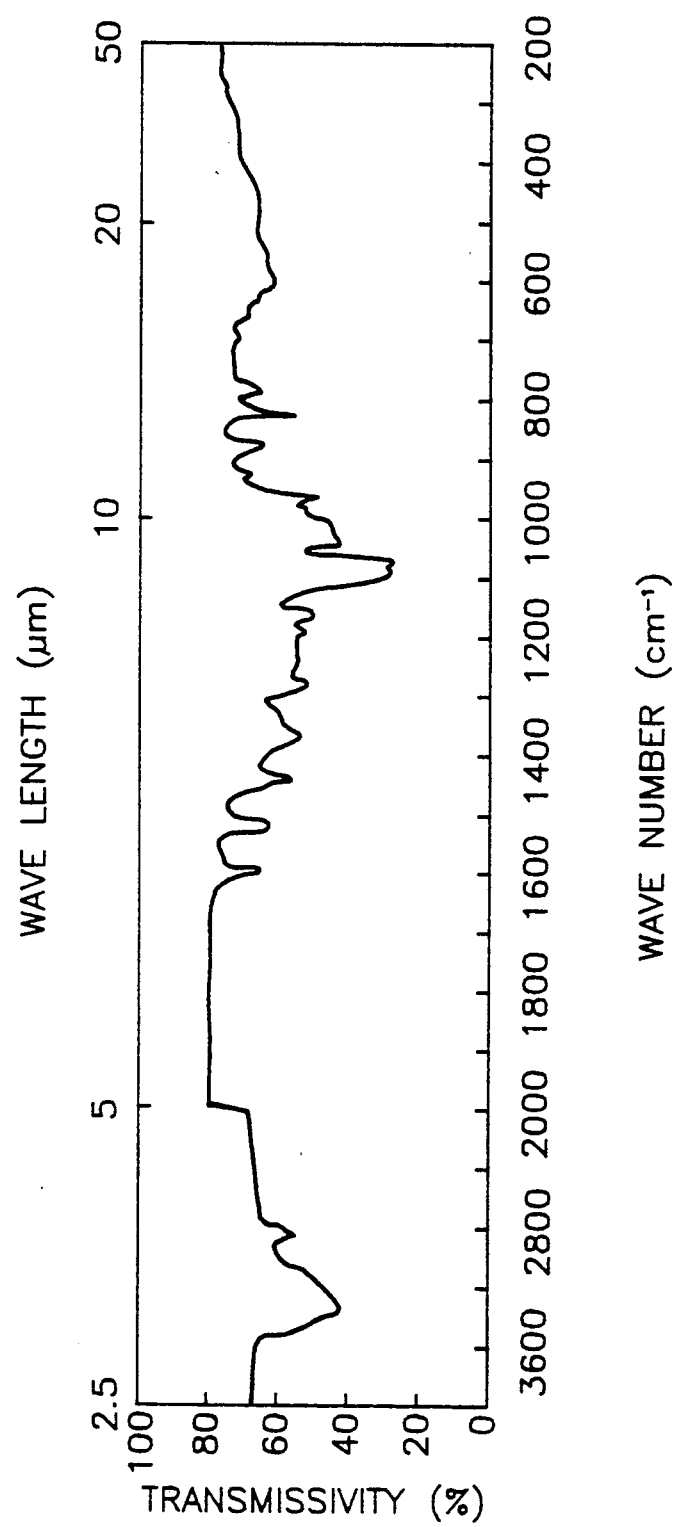

IR (KBr tablet): Shown in FIG. 8.

¹H-NMR (d-acetone, TMS internal standards, ppm): 6.7–7.0 (3H), 5.45 (1H), 4.31 (1H), 4.20 (1H), 3.6–3.8 (2H), 3.3–3.5 (5H), 3.28 (1H).

EXAMPLE 5

This example shows the results of a test on the toxicity and pharmacological characteristics of the compounds of the present invention. As the compounds of the present invention methyl-4,6-O-(3',4'-dihydroxybenzylidene)-α-D-glucopyranoside [(Ib₁)] and methyl-4,6-O-(3',4'-dibenzoyloxybenzylidene)-α-D-glucopyranoside [(Ia₁)] were used as test samples. As a control, protocatechualdehyde (PAL) was employed.

(1) ACUTE TOXICITY

Groups each comprising 5 Jcl:ICR female mice, after oral and intraperitoneal administration, were observed for 7 days, and their LD₅₀ values were determined by the Litchfield-Wilcoxon method.

The prescribed amounts of the test drugs dispersed in 0.3% CMC aqueous solution at a rate of 20 mg/ml for oral administration and the test drugs dissolved in 10% ethanol isotonic sodium chloride solution as a rate of 200 mg/ml for intraperitoneal administration were applied using gastric probes and syringes, respectively. The results are shown in Table 1.

TABLE 1

| Group | LD₅₀ mg/kg | |
|---|---|---|
| | Oral Administration | Intraperitoneal Administration |
| (Ib₁) | >4000 | >3000 |
| (Ia₁) | >4000 | 1900 |
| PAL | 1503 | 404 |

(2) GRANULOMA GROWTH INHIBITING EFFECT

Effects of inhibiting granuloma growth were investigated by the method proposed by Fujimura et al. [Ōyō Yakuri, 19 (3), 329 (1980)], using five-week old male Donryu rats. As paper disks, filter papers measuring 13 mm⌀ and 28 mg and soaked in 29% CMC solution (containing 0.1 mg/ml of 1 million unit dihydroxystreptomycin and penicillin, respectively) were used. A paper disk was implanted subcutaneously in the back of the rat under anesthesia. The test drugs dispersed in 0.3% CMC solutions were administered orally for 10 days; then, on the 11th day the granulomas were removed and their weights were measured. To the control group were administered the original 0.3% CMC solution containing no test drug.

As shown in Table 2, the results of this test indicated that the compounds of the present invention inhibit granuloma growth with a dosage smaller than that of PAL.

According to a reference (DRUGS IN JAPAN-(ETHICAL DRUGS), 9th Edition (1985), YAKUGYO JIHO CO., LTD., p.105), the LD₅₀ value of indomethacin, which was used as a positive control in this test, is 30.2 mg/kg for male mice and 29 mg/kg for male rats, and therefore, indomethacin is more toxic than both PAL and the compounds of the present invention.

Other compounds of the present invention obtained in accordance with the aforementioned Examples 2–4 also indicated a similar effect of inhibiting granuloma growth.

TABLE 2

| Group | Dosage (mg/kg/day) | No. of rats | Granuloma | |
|---|---|---|---|---|
| | | | Dry weight (mg) (mean) | Inhibition rate (%) |
| Control | — | 4 | 131.9 | — |
| Compounds of the present invention | | | | |
| (Ib₁) | 10 | 6 | 91.4 | 30.7 |
| | 50 | 6 | 66.0 | 50.0 |
| (Ia₁) | 10 | 4 | 92.6 | 29.8 |
| | 50 | 6 | 74.3 | 43.7 |
| Positive control Indomethacin | 3 | 5 | 71.3 | 45.9 |
| PAL | 50 | 6 | 86.8 | 34.2 |

EXAMPLE 8

This examples shows the pharmaceutical preparation of compounds of the present invention.

| | |
|---|---|
| Compound of the present invention [methyl-4,6-O-(3',4'-dihydroxybenzylidene)-α-D- | 10 weight parts |

| | |
|---|---|
| glucopyranoside] | |
| Heavy magnesium oxide | 15 weight parts |
| Lactose | 75 weight parts | were evenly mixed to obtain powder. This powder was placed in capsules to provide capsule preparations.

What is claimed is:

1. Saccharide derivatives of protocatechualdehyde represented by the formula (I):

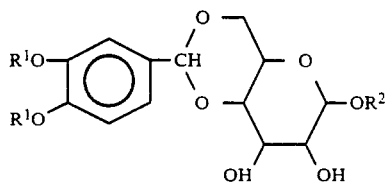
(I)

wherein $R^1$ represents a hydrogen atom or a benzoyl group; and $R^2$ represents an alkyl group.

2. Methods for preparing saccharide derivatives of protocatechualdehyde represented by the formula (I):

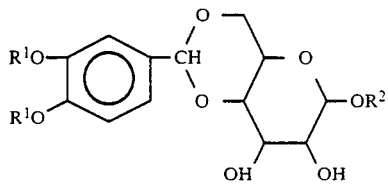
(I)

wherein $R^1$ represents a hydrogen atom or a benzoyl group and $R^2$ represents an alkyl group, wherein an acetalized compound derived from acetalization of 3,4-dibenzoyloxybenzaldehyde of the formula (II):

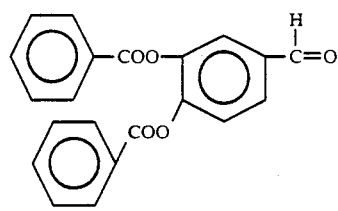
(II)

with a lower alcohol is reacted with a saccharide derivative represented by the formula (III):

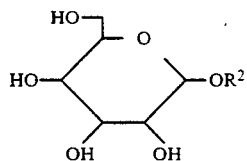
(III)

wherein $R^2$ represents an alkyl group, and furthermore, an ammonolysis is carried out when necessary.

3. Method for preparing saccharide derivatives of protocatechualdehyde according to claim 2, wherein the above acetalized compound and the saccharide derivative represented by the formula (III) are reacted in an organic solvent in the presence of an acid catalyst.

4. Method for preparing saccharide derivatives of protocatechualdehyde according to claim 2 or 3, wherein the reaction is carried out at an initial temperature of 55°–65° C., which is subsequently raised to 80°–100° C.

5. Antiflammatory agent containing pharmaceutically acceptable carriers and/or adjuvants, and as an active compound, the saccharide derivatives of protocatechualdehyde represented by the formula (1):

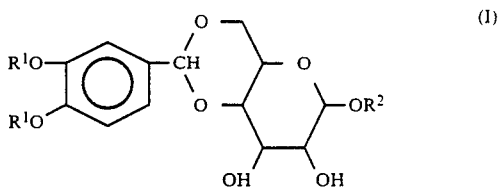
(I)

wherein $R^1$ represents a hydrogen atom or a benzoyl group, and $R^2$ represents an alkyl group.

6. Pharmaceutical compositions which comprise, as an active component, saccharide derivatives of protocatechualdehyde represented by the formula (I):

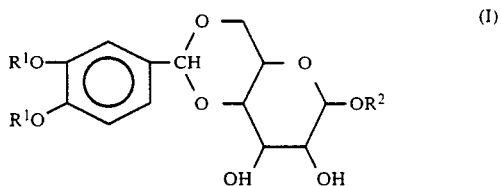
(I)

wherein $R^1$ represents a hydrogen atom or a benzoyl group, and $R^2$ represents an alkyl group, and pharmaceutically acceptable carriers and/or adjuvants.

7. Method for the treatment of inflammatory disease, which comprise administering to a patient suffering therefrom pharmaceutically effective amounts of saccharide derivatives of protocatechualdehyde represented by the formula (I):

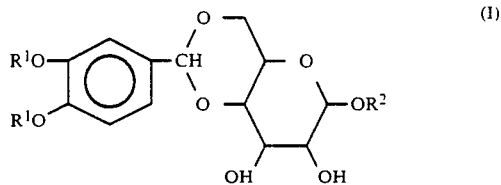
(I)

wherein $R^1$ represents a hydrogen atom or a benzoyl group, and $R^2$ represents an alkyl group.

8. The saccharide derivative of protocatechualdehyde of claim 1 which is methyl-4,6-O-(3',4'-dibenzoyloxybenzylidene-α-D-glucopyranoside.

9. The saccharide derivative of protocatechualdehyde of claim 1 which is methyl-4,6-O-(3',4'-dihydroxybenzylidene-α-D-glucopyranoside.

10. The saccharide derivative of protocatechualdehyde of claim 1 which is methyl-4,6-O-(3',4'-dibenzoyloxybenzylidene-α-D-galactopyranoside.

11. The saccharide derivative of protocatechualdehyde of claim 1 which is methyl-4,6-O-(3',4'-dihydroxybenzylidene-α-D-galactopyranoside.

12. The saccharide derivative of protocatechualdehyde of claim 1 which is methyl-4,6-O-(3',4'-dibenzoyloxybenzylidene-α-D-mannopyranoside.

13. The saccharide derivative of protocatechualdehyde of claim 1 which is methyl-4,6-O-(3',4'-dihydroxybenzylidene-α-D-mannopyranoside.

14. The saccharide derivative of protocatechualdehyde of claim 1 which is methyl-4,6-O-(3',4'-dibenzoyloxybenzylidene-β-D-glucopyranoside.

15. The saccharide derivative of protocatechualdehyde of claim 1 which is methyl-4,6-O-(3',4'-dihydroxybenzylidene-β-D-glucopyranoside.

16. The saccharide derivative of protocatechualdehyde of claim 1 which is methyl-4,6-O-(3',4'-dibenzoyloxybenzylidene-β-D-galactopyranoside.

17. The saccharide derivative of protocatechualdehyde of claim 1 which is methyl-4,6-O-(3',4'-dihydroxybenzylidene-β-D-galactopyranoside.

18. The saccharide derivative of protocatechualdehyde of claim 1 which is methyl-4,6-O-(3',4'-dibenzoyloxybenzylidene-β-D-mannopyranoside.

19. The saccharide derivative of protocatechualdehyde of claim 1 which is methyl-4,6-O-(3',4'-dihydroxybenzylidene-β-D-mannopyranoside.

20. The pharmaceutical composition of claim 6 wherein the active component is methyl-4,6-O-(3',4'-dibenzoyloxybenzylidene-α-D-glucopyranoside.

21. The pharmaceutical composition of claim 6 wherein the active component is methyl-4,6-O-(3',4'-dihydroxybenzylidene-α-D-glucopyranoside.

22. The pharmaceutical composition of claim 6 wherein the active component is methyl-4,6-O-(3',4'-dibenzoyloxybenzylidene-α-D-galactopyranoside.

23. The pharmaceutical composition of claim 6 wherein the active component is methyl-4,6-O-(3',4'-dihydroxybenzylidene-α-D-galactopyranoside.

24. The pharmaceutical composition of claim 6 wherein the active component is methyl-4,6-O-(3',4'-dibenzoyloxybenzylidene-α-D-mannopyranoside.

25. The pharmaceutical composition of claim 6 wherein the active component is methyl-4,6-O-(3',4'-dihydroxybenzylidene-α-D-mannopyranoside.

26. The pharmaceutical composition of claim 6 wherein the active component is methyl-4,6-O-(3',4'-dibenzoyloxybenzylidene-β-D-glucopyranoside.

27. The pharmaceutical composition of claim 6 wherein the active component is methyl-4,6-O-(3',4'-dihydroxybenzylidene-β-D-glucopyranoside.

28. The pharmaceutical composition of claim 6 wherein the active component is methyl-4,6-O-(3',4'-dibenzoyloxybenzylidene-β-D-galactopyranoside.

29. The pharmaceutical composition of claim 6 wherein the active component is methyl-4,6-O-(3',4'-dihydroxybenzylidene-β-D-galactopyranoside.

30. The pharmaceutical composition of claim 6 wherein the active component is methyl-4,6-O-(3',4'-dibenzoyloxybenzylidene-β-D-mannopyranoside.

31. The pharmaceutical composition of claim 6 wherein the active component is methyl-4,6-O-(3',4'-dihydroxybenzylidene-β-D-mannopyranoside.

* * * * *

UNITED STATES PATENT AND TRADEMARK OFFICE
CERTIFICATE OF CORRECTION

PATENT NO. : 5,120,835
DATED : June 9, 1992
INVENTOR(S) : Kazuyoshi Inada, et al It is certified that error appears in the above-identified patent and that said Letters Patent is hereby corrected as shown below:

On the Title Page item [57]

IN THE ABSTRACT:

line 2, "t,0010" should read:

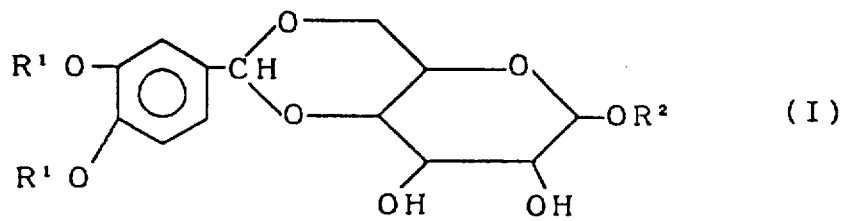

(I)

Column 1, line 24; "does" should read --dose--
line 62; "60" should read -- α --
Column 2, lines 61,63,65 and 67; and
Column 3, lines 1 and 3; "-60-" should read --)-α- --
Column 3, line 3; "n-propyl- should read --n-butyl- --
Column 12, line 34; "-4,60-" should read -- -4,6-0- --
Column 12, line 35; "dene-α-D-" should read --dene)-α-D- --
Column 16, line 60; "Example 8" should read --Example 6--

UNITED STATES PATENT AND TRADEMARK OFFICE
CERTIFICATE OF CORRECTION

PATENT NO. : 5,120,835
DATED : June 9, 1992
INVENTOR(S) : Kazuyoshi Inada, et. al.

It is certified that error appears in the above-indentified patent and that said Letters Patent is hereby corrected as shown below:

Column 18, claim 5, line 3, "compound" should read --component--.

Column 19, claim 8-31, line 3, that portion of the name reading "benzylidene-" should read --benzylident)- --.

Signed and Sealed this

Twenty-eighth Day of September, 1993

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,120,835

DATED : June 9, 1992

INVENTOR(S) : Kazuyoshi Inada, et al

It is certified that error appears in the above-identified patent and that said Letters Patent is hereby corrected as shown below:

On the Title Page item [57]

IN THE ABSTRACT:

line 2, "t,0010" should read:

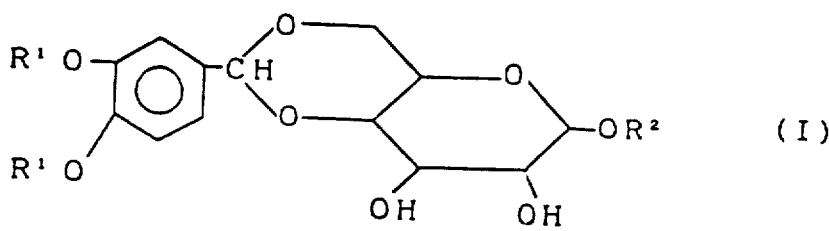

Column 1, line 24; "does" should read --dose--
        line 62; "60" should read -- α --
Column 2, lines 61,63,65 and 67; and
Column 3, lines 1 and 3; "-60-" should read --)-α- --
Column 3, line 3; "n-propyl- should read --n-butyl- --
Column 12, line 34; "-4,60-" should read -- -4,6-0- --
Column 12, line 35; "dene-α-D-" should read --dene)-α-D- --
Column 16, line 60; "Example 8" should read --Example 6--

UNITED STATES PATENT AND TRADEMARK OFFICE
CERTIFICATE OF CORRECTION

PATENT NO. : 5,120,835
DATED : June 9, 1992
INVENTOR(S) : Kazuyoshi Inada, et. al.

It is certified that error appears in the above-indentified patent and that said Letters Patent is hereby corrected as shown below:

Column 18, claim 5, line 3, "compound" should read --component--.

Column 19, claim 8-31, line 3, that portion of the name reading "benzylident)-" should read --benzylidene)- --.

This certificate supersedes Certificate of Correction issued Sept. 28, 1993.

Signed and Sealed this

Twenty-sixth Day of April, 1994

Attest:

BRUCE LEHMAN

*Attesting Officer*   *Commissioner of Patents and Trademarks*